United States Patent [19]

Krämer et al.

[11] 4,360,529
[45] Nov. 23, 1982

[54] COMBATING FUNGI WITH TRISUBSTITUTED BENZYL OXIME ETHERS

[75] Inventors: Wolfgang Krämer; Hans-Joachim Knops, both of Wuppertal; Karl H. Büchel, Burscheid; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 201,863

[22] Filed: Oct. 29, 1980

[30] Foreign Application Priority Data

Nov. 3, 1979 [DE] Fed. Rep. of Germany ....... 2944446

[51] Int. Cl.³ .............. A01N 43/64; A01N 55/02; C07D 249/08; C07F 1/08
[52] U.S. Cl. ............................ 424/269; 424/245; 424/232; 548/101; 548/262
[58] Field of Search ............. 548/101, 262; 424/245, 424/269

[56] References Cited

U.S. PATENT DOCUMENTS 4,264,772 4/1981 Kramer et al. ................ 548/101

FOREIGN PATENT DOCUMENTS

| 4917 | 4/1979 | European Pat. Off. ............ 548/262 |
| 2723942 | 12/1978 | Fed. Rep. of Germany ...... 548/262 |
| 2816816 | 10/1979 | Fed. Rep. of Germany ...... 548/262 |

*Primary Examiner*—Alton D. Rollins
*Attorney, Agent, or Firm*—Sprung, Horn, Kramer & Woods

[57] ABSTRACT

Combating fungi with a trisubstituted benzyl oxime ether of the formula

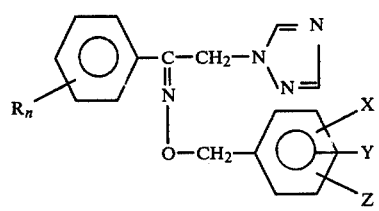

in which
R is halogen, alkyl or halogenoalkyl,
n is 1, 2 or 3, and
X, Y and Z each independently is alkyl, alkoxy or halogen, or Y and Z together are methylenedioxy, or a physiologically acceptable acid-addition salt or metal-salt complex thereof.

11 Claims, No Drawings

COMBATING FUNGI WITH TRISUBSTITUTED BENZYL OXIME ETHERS

The present invention relates to certain new trisubstituted benzyl oxime ethers, to a process for their preparation and to their use as fungicides.

It has already been disclosed that certain substituted benzyl oxime ethers, such as, in particular, dichlorobenzyl oxime ethers, have fungicidal properties (see DE-OS (German Published Specification) No. 2,723,942). However, their action is not always satisfactory in certain fields of indication, and especially when small amounts and low concentrations are applied.

The present invention now provides, as new compounds, the trisubstituted benzyl oxime ethers of the general formula

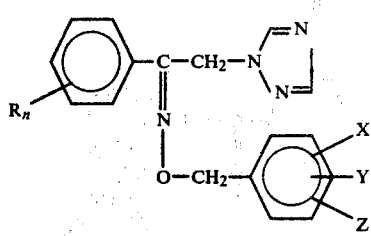

in which
R represents halogen, alkyl or halogenoalkyl,
n represents 1, 2 or 3 and
X, Y and Z are selected independently from one another and each represent alkyl, alkoxy or halogen, or
Y and Z together represent methylenedioxy,
and physiologically acceptable acid addition salts and metal salt complexes thereof.

The compounds of the formula (I) can exist in the syn-form or anti-form, and they are predominantly obtained as mixtures of the two forms.

The trisubstituted benzyl oxime ethers of the formula (I) have good fungicidal properties. Surprisingly, the compounds according to the invention exhibit a considerably more powerful action than the dichlorobenzyl oxime ethers known from the state of the art, which are the most closely related compounds chemically and from the point of view of their action. The substances according to the invention thus represent an enrichment of the art.

The formula (I) provides a general definition of the trisubstituted benzyl oxime ethers according to the invention.
Preferably, in this formula,
R represents fluorine, chlorine, bromine, straight-chain or branched alkyl with 1 to 4 carbon atoms (especially methyl) or halogenoalkyl with 1 to 2 carbon atoms and 1 to 3 halogen atoms (especially fluorine and chlorine atoms, trifluoromethyl being mentioned as an example),
X, Y and Z are identical or different and each represent straight-chain or branched alkyl or alkoxy with in either case 1 to 4 carbon atoms (especially methyl or methoxy), fluorine, chlorine or bromine, or
Y and Z together alternatively represent methylenedioxy, and
n represents 1 or 2.

Those trisubsituted benzyl oxime ethers of the formula (I) in which X, Y and Z do not simultaneously represent halogen are particularly preferred.

The following compounds of the general formula (I) may be mentioned specifically, in addition to the compounds mentioned later in the preparative examples:

TABLE 1 (I)

| $R_n$ | X | Y | Z |
|---|---|---|---|
| 2-Cl | 2-Cl | 3-Cl | 6-Cl |
| 2-Cl | 2-OCH$_3$ | 4-OCH$_3$ | 6-OCH$_3$ |
| 2-Cl | 2-OCH$_3$ | 3-OCH$_3$ | 4-OCH$_3$ |
| 2-Cl | 2-OCH$_3$ | 4-OCH$_3$ | 5-OCH$_3$ |
| 2-Cl | 3-OCH$_3$ | 4-OCH$_3$ | 5-OCH$_3$ |
| 2-Cl | 2-CH$_3$ | 3-CH$_3$ | 4-OCH$_3$ |
| 2-Cl | 2-CH$_3$ | 5-CH$_3$ | 4-OCH$_3$ |
| 2-Cl | 2-Cl | 4,5-O—CH$_2$—O— | |
| 2,4-Cl$_2$ | 2-OCH$_3$ | 4-OCH$_3$ | 6-OCH$_3$ |
| 2,4-Cl$_2$ | 2-OCH$_3$ | 3-OCH$_3$ | 4-OCH$_3$ |
| 2,4-Cl$_2$ | 2-OCH$_3$ | 4-OCH$_3$ | 5-OCH$_3$ |
| 2,4-Cl$_2$ | 3-OCH$_3$ | 4-OCH$_3$ | 5-OCH$_3$ |
| 2,4-Cl$_2$ | 2-CH$_3$ | 3-CH$_3$ | 4-OCH$_3$ |
| 2,4-Cl$_2$ | 2-CH$_3$ | 5-CH$_3$ | 4-OCH$_3$ |
| 2,4-Cl$_2$ | 2-Cl | 4,5-O—CH$_2$—O— | |
| 2-CH$_3$,4-Cl | 2-OCH$_3$ | 4-OCH$_3$ | 6-OCH$_3$ |
| 2-CH$_3$,4-Cl | 2-OCH$_3$ | 3-OCH$_3$ | 4-OCH$_3$ |
| 2-CH$_3$,4-Cl | 2-OCH$_3$ | 4-OCH$_3$ | 5-OCH$_3$ |
| 2-CH$_3$,4-Cl | 3-OCH$_3$ | 4-OCH$_3$ | 5-OCH$_3$ |
| 2-CH$_3$,4-Cl | 2-CH$_3$ | 3-CH$_3$ | 4-CH$_3$ |
| 2-CH$_3$,4-Cl | 2-CH$_3$ | 5-CH$_3$ | 4-OCH$_3$ |
| 2-CH$_3$,4-Cl | 2-Cl | 4,5-O—CH$_2$—O— | |
| 2-CH$_3$,4-Cl | 2-Cl | 4-Cl | 6-Cl |
| 2-CH$_3$,4-Cl | 2-Cl | 3-Cl | 6-Cl |
| 2-CH$_3$,4-Cl | 2-CH$_3$ | 4-CH$_3$ | 6-CH$_3$ |
| 2-Cl,4-CH$_3$ | 2-OCH$_3$ | 4-OCH$_3$ | 6-OCH$_3$ |
| 2-Cl,4-CH$_3$ | 2-OCH$_3$ | 3-OCH$_3$ | 4-OCH$_3$ |
| 2-Cl,4-CH$_3$ | 2-OCH$_3$ | 4-OCH$_3$ | 5-OCH$_3$ |
| 2-Cl,4-CH$_3$ | 3-OCH$_3$ | 4-OCH$_3$ | 5-OCH$_3$ |
| 2-Cl,4-CH$_3$ | 2-CH$_3$ | 3-CH$_3$ | 4-OCH$_3$ |
| 2-Cl,4-CH$_3$ | 2-CH$_3$ | 5-CH$_3$ | 4-OCH$_3$ |
| 2-Cl,4-CH$_3$ | 2-Cl | 4,5-O—CH$_2$—O— | |
| 2-Cl,4-CH$_3$ | 2-Cl | 4-Cl | 6-Cl |
| 2-Cl,4-CH$_3$ | 2-Cl | 3-Cl | 6-Cl |
| 2-Cl,4-CH$_3$ | 2-CH$_3$ | 4-CH$_3$ | 6-CH$_3$ |
| 2-CF$_3$,4-Cl | 2-OCH$_3$ | 4-OCH$_3$ | 6-OCH$_3$ |
| 2-CF$_3$,4-Cl | 2-OCH$_3$ | 3-OCH$_3$ | 4-OCH$_3$ |
| 2-CF$_3$,4-Cl | 2-OCH$_3$ | 4-OCH$_3$ | 5-OCH$_3$ |
| 2-CF$_3$,4-Cl | 3-OCH$_3$ | 4-OCH$_3$ | 5-OCH$_3$ |
| 2-CF$_3$,4-Cl | 2-CH$_3$ | 3-CH$_3$ | 4-OCH$_3$ |
| 2-CF$_3$,4-Cl | 2-CH$_3$ | 5-CH$_3$ | 4-OCH$_3$ |
| 2-CF$_3$,4-Cl | 2-Cl | 4,5-O—CH$_2$—O— | |
| 2-CF$_3$,4-Cl | 2-Cl | 4-Cl | 6-Cl |
| 2-CF$_3$,4-Cl | 2-Cl | 3-Cl | 6-Cl |
| 2-CF$_3$,4-Cl | 2-CH$_3$ | 4-CH$_3$ | 6-CH$_3$ |
| 2-CH$_3$,4-Br | 2-OCH$_3$ | 4-OCH$_3$ | 6-OCH$_3$ |
| 2-CH$_3$,4-Br | 2-OCH$_3$ | 3-OCH$_3$ | 4-OCH$_3$ |
| 2-CH$_3$,4-Br | 2-OCH$_3$ | 4-OCH$_3$ | 5-OCH$_3$ |
| 2-CH$_3$,4-Br | 3-OCH$_3$ | 4-OCH$_3$ | 5-OCH$_3$ |
| 2-CH$_3$,4-Br | 2-CH$_3$ | 3-CH$_3$ | 4-OCH$_3$ |
| 2-CH$_3$,4-Br | 2-CH$_3$ | 5-CH$_3$ | 4-OCH$_3$ |
| 2-CH$_3$,4-Br | 2-Cl | 4,5-O—CH$_2$—O— | |
| 2-CH$_3$,4-Br | 2-Cl | 4-Cl | 6-Cl |
| 2-CH$_3$,4-Br | 2-Cl | 3-Cl | 6-Cl |
| 2-CH$_3$,4-Br | 2-CH$_3$ | 4-CH$_3$ | 6-CH$_3$ |
| 2-Cl,6-Cl | 2-OCH$_3$ | 4-OCH$_3$ | 6-OCH$_3$ |
| 2-Cl,6-Cl | 2-OCH$_3$ | 3-OCH$_3$ | 4-OCH$_3$ |
| 2-Cl,6-Cl | 2-OCH$_3$ | 4-OCH$_3$ | 5-OCH$_3$ |
| 2-Cl,6-Cl | 3-OCH$_3$ | 4-OCH$_3$ | 5-OCH$_3$ |
| 2-Cl,6-Cl | 2-CH$_3$ | 3-CH$_3$ | 4-OCH$_3$ |
| 2-Cl,6-Cl | 2-CH$_3$ | 5-CH$_3$ | 4-OCH$_3$ |

TABLE 1-continued

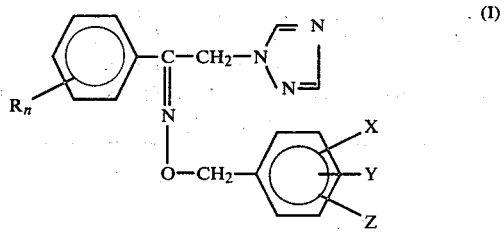

| $R_n$ | X | Y | Z |
|---|---|---|---|
| 2-Cl,6-Cl | 2-Cl | 4,5-O—CH$_2$—O— | |
| 2-Cl,6-Cl | 2-Cl | 4-Cl | 6-Cl |
| 2-Cl,6-Cl | 2-Cl | 3-Cl | 6-Cl |
| 2-Cl,6-Cl | 2-CH$_3$ | 4-CH$_3$ | 6-CH$_3$ |
| 2-CH$_3$ | 2-OCH$_3$ | 4-OCH$_3$ | 6-OCH$_3$ |
| 2-CH$_3$ | 2-OCH$_3$ | 3-OCH$_3$ | 4-OCH$_3$ |
| 2-CH$_3$ | 2-OCH$_3$ | 4-OCH$_3$ | 5-OCH$_3$ |
| 2-CH$_3$ | 3-OCH$_3$ | 4-OCH$_3$ | 5-OCH$_3$ |
| 2-CH$_3$ | 2-CH$_3$ | 3-CH$_3$ | 4-OCH$_3$ |
| 2-CH$_3$ | 2-CH$_3$ | 5-CH$_3$ | 4-OCH$_3$ |
| 2-CH$_3$ | 2-Cl | 4,5-O—CH$_2$—O— | |
| 2-CH$_3$ | 2-Cl | 4-Cl | 6-Cl |
| 2-CH$_3$ | 2-Cl | 3-Cl | 6-Cl |
| 2-CH$_3$ | 2-CH$_3$ | 4-CH$_3$ | 6-CH$_3$ |

The invention also provides a process for the preparation of a trisubstituted benzyl oxime ether of the formula (I), or an acid addition salt or metal salt complex thereof, in which (a) an oxime of the general formula

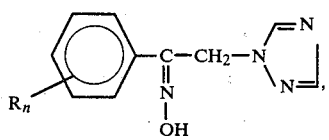

in which
R and n have the meanings indicated above, is reacted with a benzyl halide of the general formula

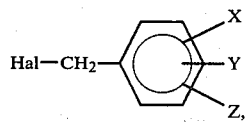

in which
X, Y and Z have the meanings indicated above and
Hal represents chlorine or bromine,
if appropriate in the presence of a strong base and in the presence of a diluent, or (b) an ω-halogeno-acetophenone oxime ether of the general formula

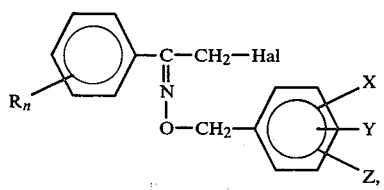

in which
R, n, X, Y and Z have the meanings indicated above and

Hal represents chlorine or bromine,
is reacted with 1,2,4-triazole in the presence of an acid-binding agent and in the presence of a diluent, and, if required, an acid or a metal salt is added onto the compound obtained by process variant (a) or (b).

If, for example, 1-(2,4-dichlorophenyl)-1-oximino-2-(1,2,4-triazol-1-yl)-ethane and 2,4,6-trichlorobenzyl chloride are used as starting substances in process variant (a), the course of the reaction can be represented by the following equation:

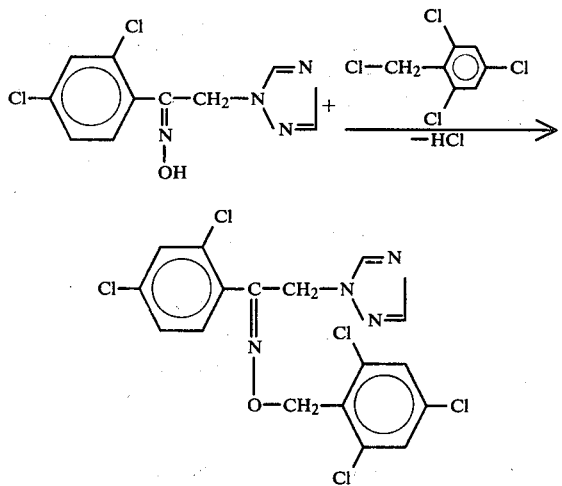

If, for example, ω-chloro-2,4-dichloroacetophenone oxime O-(2,4,6-trimethylbenzyl) ether and 1,2,4-triazole are used as starting substances in process variant (b), the course of the reaction can be represented by the following equation:

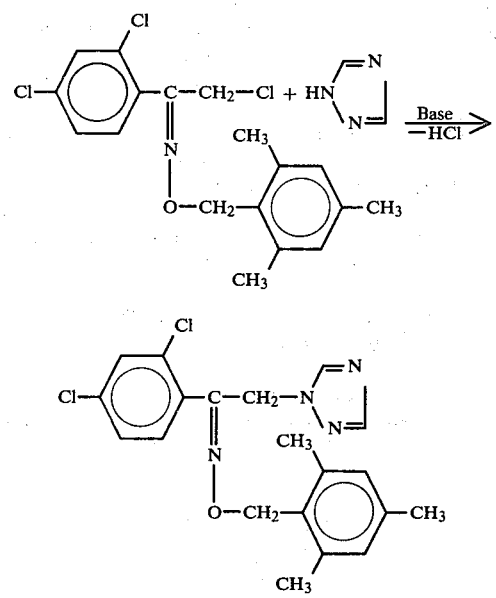

The formula (II) provides a general definition of the oximes to be used as starting substances in carrying out process variant (a). In this formula, R preferably has those meanings which have already been mentioned as preferred in connection with the description of the substances of the formula (I).

The oximes of the formula (II) are known (see DE-OS (German Published Specification) No. 2,723,942 and DE-OS (German Published Specification) No. 2,657,578), and they are obtained by a process in which, in a first stage, ω-halogen-acetophenones are reacted with 1,2,4-triazole in the presence of an inert organic solvent and in the presence of an acid-binding agent at temperatures between 20° and 120° C., and the ω-(1,2,4-triazol-1-yl)-acetophenones formed are reacted, in a second stage, with hydroxylamine in the presence of a solvent, preferably an alcohol, at 50° to 100° C., the hydroxylamine preferably being employed as the hydrochloride in the presence of an acid-binding agent.

The formula (III) provides a general definition of the benzyl halides also to be used as starting substances for process variant (a). In this formula, X, Y and Z preferably have those meanings which have already been mentioned as preferred in connection with the description of the substances of the formula (I).

The benzyl halides of the formula (III) are generally known compounds of organic chemistry.

The formula (IV) provides a general definition of the ω-halogeno-acetophenone oxime ethers to be used as starting substances in carrying out process variant (b) according to the invention. In this formula, R, X, Y and Z preferably have those meanings which have already been mentioned as preferred in connection with the description of the substances of the formula (I).

The ω-halogeno-acetophenone oxime ethers of the formula (IV) have not hitherto been disclosed in the literature. However, they can be obtained by a new process which is the subject of an earlier patent application which has not yet been published (German Patent Application No. P 2907 872.9, filed Mar. 1, 1979. The substances of the formula (IV) are obtained by a process in which ω-halogeno-acetophenones of the general formula

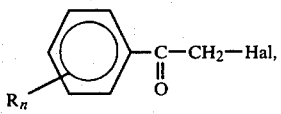 (V)

in which

R, n and Hal have the meanings indicated above, are reacted with hydroxylamine ethers of the general formula

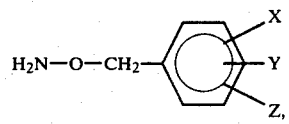 (VI)

in which

Y, X and Z have the meanings indicated above, in the presence of a diluent, preferably an alcohol or an aqueous alcohol, at a temperature between 50° and 100° C., the ethers of the formula (VI) preferably being employed in the form of their hydrochlorides in the presence of an acid-binding agent.

The following acids can preferably be used for the preparation of physiologically acceptable acid addition salts of the compounds of the formula (I): hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid), and sulphonic acids (for example p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII can preferably be used for the preparation of metal salt complexes of the compounds of the formula (I), examples of metals which may be mentioned being copper, zinc, manganese, magnesium, tin, iron and nickel. Preferred anions of the salts are those which are derived from the following acids: hydrogen halide acids (for example hydrochloric acid and hydrobromic acid), phosphoric acid, nitric acid and sulphuric acid.

The metal salt complexes of compounds of the formula (I) can be obtained in a simple manner by customary processes, for example by dissolving the metal salt in alcohol, for example ethanol, and adding the solution to the compound of the formula (I). The metal salt complexes can be purified in a known manner, for example by filtration, isolation and, if appropriate, recrystallization.

Possible diluents for the reaction in process variant (a) are inert organic solvents. These include, as preferences, ethers, such as tetrahydrofuran and dioxane; aromatic hydrocarbons, such as toluene and benzene; in individual cases also chlorinated hydrocarbons, such as chloroform, methylene chloride or carbon tetrachloride; hexamethylphosphoric acid triamide; acid amides, such as dimethylformamide; and sulphoxides, such as dimethylsulphoxide.

If appropriate, the reaction in process variant (a) is carried out in the presence of a strong base. Strong bases include, as preferences, alkali metal amides, hydrides, hydroxides and carbonates, for example sodium amide, carbonate, hydroxide or hydride and potassium amide, carbonate, hydroxide or hydride, and quaternary ammonium hydroxides and phosphonium hydroxides, for example tetramethyl-ammonium hydroxide, benzyl-trimethyl-ammonium hydroxide or dibenzyl-dimethyl-ammonium hydroxide and tetraphenyl-phosphonium hydroxide or methyl-triphenyl-phosphonium hydroxide.

The reaction temperatures can be varied within a substantial range in process variant (a). In general, the reaction is carried out between 20° and 150° C., preferably at room temperature. In individual cases, it is advantageous to carry out the reaction at the boiling point of the solvent, for example between 60° and 100° C.

In carrying out process variant (a), 1 to 3 mols of benzyl halide of the formula (III) are preferably employed per mol of oxime of the formula (II). To isolate the end products, the reaction mixture is freed from the solvent and water and an organic solvent is added to the residue. The organic phase is separated off, worked up in the customary manner and purified, and the salt or metal salt complex is optionally prepared.

In a preferred embodiment of process variant (a), the reaction according to the invention is carried out in a two-phase system, for example aqueous sodium hydroxide solution or potassium hydroxide solution/toluene or methylene chloride, with the addition of 0.01-1 mol of a phase-transfer catalyst, for example an ammonium or phosphonium compound, the ethylates being formed in the organic phase or at the interface and reacting with the halides present in the organic phase.

Preferred diluents for the reaction in process variant (b) are inert organic solvents. These include nitriles, such as acetonitrile; alcohols, such as ethanol; ethers, such as tetrahydrofuran or dioxane; aromatic hydrocarbons, such as toluene and benzene; formamides, such as dimethylformamide; and halogenated hydrocarbons, such as methylene chloride, carbon tetrachloride or chloroform.

The reaction in process variant (b) is carried out in the presence of an acid-binding agent. It is possible to add any of the inorganic or organic acid-binding agents which can customarily be used, such as alkali metal carbonates, for example sodium carbonate and potassium carbonate; or such as lower tertiary alkylamines, cycloalkylamines or aralkylamines, for example triethylamine, N,N-dimethylcyclohexylamine and N,N-dimethylbenzylamine. An appropriate excess of 1,2,4-triazole is also possible.

The reaction temperatures can be varied within a substantial range in process variant (b). In general, the reaction is carried out between 0° and 150° C., preferably between 60° and 120° C.

For carrying out process variant (b), 1 to 2 mols of 1,2,4-triazole and 1 to 2 mols of acid-binding agent are preferably employed per mol of the compounds of the formula (IV). The compounds of the formula (I) are isolated by customary methods. Since the substances of the formula (I) are obtained in the form of oils, they are preferably isolated as salts, in particular as hydrochlorides or nitrates.

In a particular embodiment of process variant (b), it is also possible to follow a procedure in which the intermediate products of the formula (IV) are first prepared and are further reacted without isolation and without changing the solvent, the end products of the formula (I) being obtained in one operation in a "one-pot process".

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating *Venturia* species, for example the apple scab caustive organism (*Fusicladium dendriticum*), *Podosphaera* species, for example the powdery mildew of apple causative organism (*Podosphaera leucotricha*) and cereal diseases, such as powdery mildew of cereal and cereal rust.

The active compounds can be converted into the customary formulations, such as solutions, emulsions, suspensions, powders, dusting agents, foams, pastes, soluble powders, granules, aerosols, suspension-emulsion concentrates, seed-treatmment powders, natural and synthetic materials impregnated with active compund, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl-naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of in general 0.001 to 50 g, preferably 0.01 to 10 g, are generally employed per kilogram of seed.

For the treatment of soil, active compound, concentrations of in general 0.00001 to 0.1% by weight, preferably 0.0001 to 0.02%, are required at the place of action.

When certain amounts are applied, the substances according to the invention also exhibit a growth-regulating action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLE

EXAMPLE 1

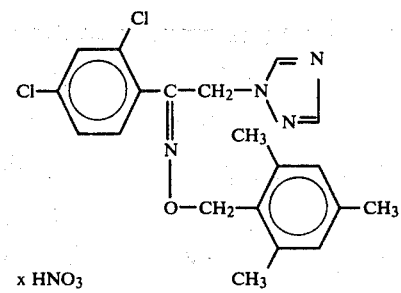

16.8 g (0.1 mol) of 2,4,6-trimethylbenzyl chloride in 20 ml of dimethylformamide were added dropwise to 27.1 g (0.1 mol) of ω-(1,2,4-triazol-1-yl)-oximino-2,4-dichloroacetophenone and 14 g (0.1 mol) of potassium carbonate in 100 ml of dimethylformamide at 40° to 60° C. The reaction mixture was subsequently stirred at 50° C. for 15 hours. It was then poured onto 1,000 ml of ice-water. The aqueous phase was extracted with 500 ml of methylene chloride and the organic phase was extracted four times with 100 ml of water each time. The combined organic phases were dried over sodium sulphate, filtered and concentrated by distilling off the solvent in vacuo. The resulting oil was dissolved in 100 ml of acetone, and 18 g of 1,5-naphthalenedisulphonic acid, dissolved in 50 ml of acetone, were filtered in. The precipitate formed was filtered off and taken up in 200 ml of water/sodium bicarbonate and the mixture was extracted by shaking with 200 ml of methylene chloride. The organic phase was concentrated and the residue was dissolved in 100 ml of chloroform. 3 ml of concentrated nitric acid were added dropwise, while cooling with ice, and the precipitate was filtered off. After washing with 50 ml of petroleum ether, 21.6 g (46% of theory) of 1-(2,4-dichlorophenyl)-1-(2,4,6-trimethyl-benzyloximino)-2-(1,2,4-triazol-1-yl)-ethane nitrate of melting point 74°-78° C. were obtained.

The following compounds of the general formula

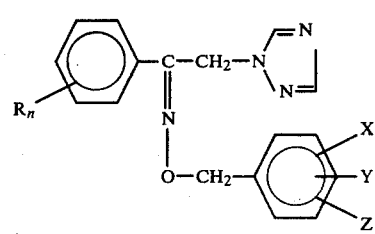

were obtained in a corresponding manner and by the processes indicated:

TABLE 2

| Compound No. | $R_n$ | X | Y | Z | Melting point (°C.) |
|---|---|---|---|---|---|
| 2 | 2,4-Cl$_2$ | 2-Cl | 4-Cl | 6-Cl | 158–62(xHNO$_3$) |
| 3 | 2,4-Cl$_2$ | 2-Cl | 5-Cl | 6-Cl | 153–60(decomp.) (xHNO$_3$) |
| 4 | 2-Cl | 2-Cl | 4-Cl | 6-Cl | 153–55(xHNO$_3$) |
| 5 | 2-Cl | 2-CH$_3$ | 4-CH$_3$ | 6-CH$_3$ | 128–30(XHNO$_3$) |
| 6 | 2,4-Cl$_2$ | 2-CH$_3$ | 4-CH$_3$ | 6-CH$_3$ | 40 |
| 7 | 2-Cl,4-CH$_3$ | 2-CH$_3$ | 4-CH$_3$ | 6-CH$_3$ | 100-07 |
| 8 | 2-CF$_3$,4-Cl | 2-CH$_3$ | 4-CH$_3$ | 6-CH$_3$ | 151 (xHNO$_3$) |

TABLE 2-continued

| Compound No. | $R_n$ | X | Y | Z | Melting point (°C.) |
|---|---|---|---|---|---|
| | | | | | (decomp.) |
| 9 | 2-CH₃,4-Cl | 2-CH₃ | 4-CH₃ | 6-CH₃ | 130–34 (decomp.) (xHNO₃) |
| 10 | 2-CH₃,4-Cl | 2-OCH₃ | 4-OCH₃ | 5-OCH₃ | 83 (decomp.) (xHNO₃) |
| 11 | 2-CH₃,4-Cl | 3-OCH₃ | 4-OCH₃ | 5-OCH₃ | 93 (decomp.) (xHNO₃) |
| 12 | 2-CH₃,4-Cl | 2-OCH₃ | 3-OCH₃ | 4-OCH₃ | 104(decomp.) (xHNO₃) |
| 13 | 2-CF₃,4-Cl | 2-OCH₃ | 4-OCH₃ | 5-OCH₃ | 80 (decomp.) (xHNO₃) |
| 14 | 2-CF₃,4-Cl | 3-OCH₃ | 4-OCH₃ | 5-OCH₃ | 121 (decomp.) (xHNO₃) |
| 15 | 2-CF₃,4-Cl | 2-OCH₃ | 3-OCH₃ | 4-OCH₃ | 103 (decomp.) (xHNO₃) |
| 16 | 2-CH₃,4-Br | 3-OCH₃ | 4-OCH₃ | 5-OCH₃ | 114 (decomp.) (xHNO₃) |
| 17 | 2-CH₃ | 2-OCH₃ | 4-OCH₃ | 5-OCH₃ | 103 (decomp.) (xHNO₃) |
| 18 | 2-CH₃ | 3-OCH₃ | 4-OCH₃ | 5-OCH₃ | 112–17 (xHNO₃) |
| 19 | 2-CH₃,4-Br | 2-CH₃ | 4-CH₃ | 6-CH₃ | 143–47 (xHNO₃) |
| 20 | 2-CH₃ | 2-CH₃ | 4-CH₃ | 6-CH₃ | 106–14 (xHNO₃) |
| 21 | 2-CH₃,4-Br | 2-Cl | 4,5-O—CH₂—O— | | 116–18 (xHNO₃) |
| 22 | 2-CF₃,4-Cl | 2-CH₃ | 4-OCH₃ | 5-CH₃ | 114–19 (xHNO₃) |
| 23 | 2-CH₃,4-Cl | 2-Cl | 4,5-O—CH₂—O— | | 110–12 (decomp.) (xHNO₃) |
| 24 | 2-CF₃,4-Cl | 2-Cl | 4,5-O—CH₂—O— | | 110 (decomp.) (xHNO₃) |
| 25 | 2,4-Cl₂ | 2-Cl | 4,5-O—CH₂—O— | | 120–24 (decomp.) (xHNO₃) |
| 26 | 2-Cl | 2-Cl | 4,5-O—CH₂—O— | | 175–78 (xHCl) |
| 27 | 2,4-Cl₂ | 3-OCH₃ | 4-OCH₃ | 5-OCH₃ | oil |
| 28 | 2-Cl | 3-OCH₃ | 4-OCH₃ | 5-OCH₃ | oil |
| 29 | 2,4-Cl₂ | 2-OCH₃ | 3-OCH₃ | 4-OCH₃ | oil |
| 30 | 2-Cl | 2-OCH₃ | 3-OCH₃ | 4-OCH₃ | oil |
| 31 | 2,4-Cl₂ | 2-CH₃ | 4-OCH₃ | 5-CH₃ | oil |
| 32 | 2-CH₃,4-Br | 2-CH₃ | 4-OCH₃ | 5-CH₃ | amorphous (xHNO₃) |
| 33 | 2-CH₃, 4-Cl | 2-CH₃ | 4-OCH₄ | 5-CH₃ | Oil (xHNO₃) |
| 34 | 2-CH₃ | 2-CH₃ | 4-OCH₃ | 5-CH₃ | Oil (xHNO₃) |
| 35 | 2-CH₃, 4-Br | 2-CH₃ | 3-CH₃ | 4-OCH₃ | 106–14(decomp.) (xHNO₃) |
| 36 | 2-CH₃, 4-Cl | 2-CH₃ | 3-CH₃ | 4-OCH₃ | 128(decomp.) (xHNO₃) |
| 37 | 2-CF₃, 4-Cl | 2-CH₃ | 3-CH₃ | 4-OCH₃ | 137(decomp.) (xHNO₃) |
| 38 | 2-CH₃ | 2-CH₃ | 3-CH₃ | 4-OCH₃ | Oil (xHNO₃) |
| 39 | 2-CH₃,4-Br | 2-OCH₃ | 3-OCH₃ | 4-OCH₃ | Oil (xHNO₃) |
| 40 | 2-CH₃ | 2-OCH₃ | 3-OCH₃ | 4-OCH₃ | Oil (xHNO₃) |

The fungicidal activity of the compounds of this invention is illustrated by the following examples wherein the compounds according to the present invention are each identified by the number (given in brackets) from Example 1 hereinabove.

The known comparison compounds are identified as follows:

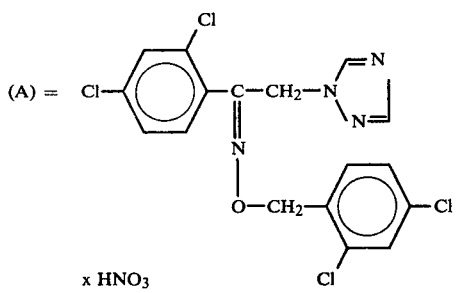

(A) = x HNO₃

-continued

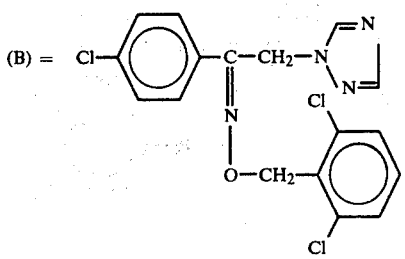

EXAMPLE 2

Fusicladium test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4-6 leaf stage were sprayed with the spray liquid until dripping wet. The plants remained in a greenhouse for 24 hours at 20 degrees C. and at a relative atmosphere humidity of 70%. They were then inoculated with an aqueous conidium suspension of the apple scab causative organism (*Fusicladium dendriticum*) and incubated for 18 hours in a humidity chamber at 18-20 degrees C. and at a relative atmospheric humidity of 100%.

The plants were then brought into a greenhouse again for 14 days.

15 days after inoculation, the infection of the seedlings were determined. The assessment data were converted to percent infection. 0% meant no infection; 100% meant that the plants were totally infected.

The active compounds, the concentrations of the active compounds and the results can be seen from the following table:

TABLE 3

| | Fusicladium test (apple)/protective |
|---|---|
| Active compound | Infection in % at an active compound concentration of 0.0025% |
| (A) | 11 |
| (B) | 40 |
| (1) | 0 |
| (2) | 0 |
| (3) | 0 |

EXAMPLE 3

Podosphaera test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4-5 leaf stage were sprayed with the spray liquid until dripping wet. The plants remained in a greenhouse for 24 hours at 20 deg. C. and at a relative atmospheric humidity of 70%. They were then inoculated by dusting the conidia of the apple powdery mildew causative organism (*Podosphaera leucotricha*) and placed in a greenhouse at a temperature of 21-23 deg. C. and at a relative atmospheric humidity of about 70%.

10 days after the inoculation, the infection of the seedlings was determined. The assessment data were converted to % infection. 0% meant no infection; 100% meant that the plants were completely infected.

The active compounds, the concentrations of the active compounds and the results can be seen from the following table:

TABLE 4

| | Podosphaera test (apple)/protective |
|---|---|
| Active compound | Infection in % at an active compound concentration of 0.0005% |
| (A) | 20 |
| (B) | 12 |
| (1) | 0 |
| (2) | 0 |
| (3) | 0 |

EXAMPLE 4

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. hordei.

After 6 days' dwell time of the plants at a temperature of 21-22 deg. C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

The active compounds, active compound concentrations in the spray liquor and degrees of infection can be seen from the table which follows:

TABLE 5

| Shoot treatment test/powdery mildew of cereal/ protective | | |
|---|---|---|
| Active compounds | Active compound concentration in the spray liquor in % by weight | Infection in % of the untreated control |
| (A) | 0.0005 | 62.5 |
| (2) | 0.0005 | 12.5 |
| (3) | 0.0005 | 33.8 |

TABLE 5-continued

Shoot treatment test/powdery mildew of cereal/ protective

| Active compounds | Active compound concentration in the spray liquor in % by weight | Infection in % of the untreated control |
|---|---|---|
| (1) | 0.0005 | 12.5 |

EXAMPLE 5

Shoot treatment test/cereal rust (leaf-destruction mycosis/protective

To produce a suitable preparation of active compound, 0.25 part by weight of active compound was taken up in 25 parts by weight of dimethylformamide and 0.06 part by weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dewmoist and were placed, for incubation, in a greenhouse for 24 hours at about 20 deg. C. and 100% relative atmospheric humidity.

After 10 days' dwell time of the plants at a temperature of 20 deg. C. and 80–90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The more active the compound, the lower was the degree of rust infection.

The active compounds, active compound concentrations in the spray liquor and degrees of infection can be seen from the table which follows:

TABLE 6

Shoot treatment test/cereal rust/protective

| Active compounds | Active compound concentration in the spray liquor in % by weight | Infection in % of the untreated control |
|---|---|---|
| (B) | 0.025 | 100 |
| (2) | 0.025 | 16.3 |
| (3) | 0.025 | 16.3 |
| (1) | 0.025 | 25.0 |

It will be understood that the specification and examples are illustrative but not limitative of the present invention and that other embodiments within the spirit and scope of the invention will suggest themselves to those skilled in the art.

We claim:

1. A trisubstituted benzyl oxime ether of the formula

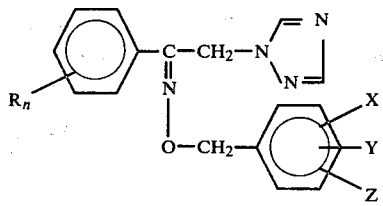

in which
R is halogen, alkyl with 1 to 4 carbon atoms or halogenoalkyl with 1 or 2 carbon atoms and 1 to 3 halogen atoms,
n is 1, 2 or 3, and
X, Y and Z each independently is alkyl or alkoxy with 1 to 4 carbon atoms, or halogen, or Y and Z together are methylenedioxy, or a physiologically acceptable acid-addition salt or metal-salt complex thereof.

2. A compund according to claim 1, in which
R is fluorine, chlorine, bromine, alkyl with 1 to 4 carbon atoms or halogenoalkyl with 1 to 2 carbon atoms and 1 to 3 halogen atoms,
n is 1 or 2, and
X, Y and Z each independently is alkyl with 1 to 4 carbon atoms, alkoxy with 1 to 4 carbon atoms, fluorine, chlorine or bromine, or
Y and Z together are methylenedioxy,
or an addition salt thereof with a hydrogen halide acid, phosphoric acid, nitric acid, sulphuric acid, a sulphonic acid or a monofunctional or bifunctional carboxylic acid, or a complex thereof with a metal salt, the metal of which is copper, zinc, manganese, magnesium, tin, iron or nickel and the anion of which is halide, phosphate, nitrate or sulphate.

3. A compound, salt or complex according to claim 1, in which
R is fluorine, chlorine, bromine, methyl or trifluoromethyl,
n is 1 or 2, and
X, Y and Z each independently is methyl, methoxy, fluorine, chlorine or bromine, or Y and Z together are methylenedioxy.

4. A compound according to claim 1 or a salt or complex thereof, wherein such compound is 1-(2,4-dichlorophenyl)-1-(2,3,6-trichloro-benzyloximino)-2-(1,2,4-triazol-1-yl)-ethane of the formula

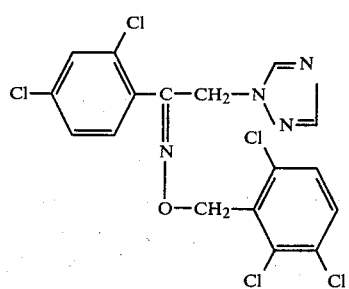

5. A compound according to claim 1 or a salt or complex thereof, wherein such compound is 1-(2-chlorophenyl)-1-(2,4,6-trichloro-benzyloximino)-2-(1,2,4-triazol-1yl)-ethane of the formula

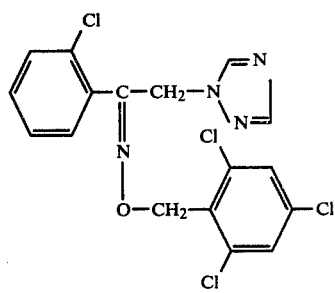

6. A compound according to claim 1 or a salt or complex thereof, wherein such compound is 1-(2-chlorophenyl)-1-(2,4,6-trimethyl-benzyloximino)-2-(1,2,4-triazol-1-yl)-ethane of the formula

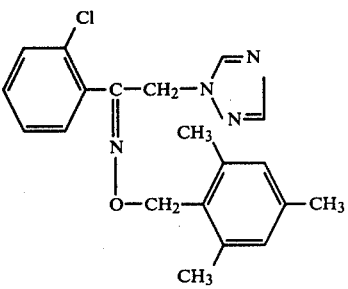

7. A compound according to claim 1 or a salt or complex thereof, wherein such compound is 1-(2,4-dichlorophenyl)-1-(2,4,6-trimethyl-benzyloximino)-2-(1,2,4-triazol-1-yl)-ethane of the formula

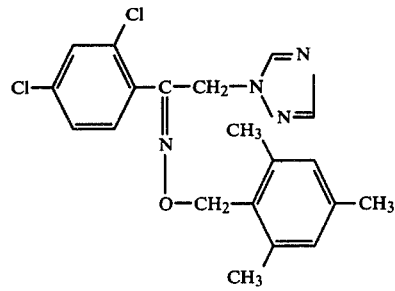

8. A compound according to claim 1 or a salt or complex thereof, wherein such compound is 1-(4-chloro-2-methylphenyl)-1-(2,4,6-trimethyl-benzyloximino)-2-(1,2,4-triazol-1-yl)-ethane of the formula

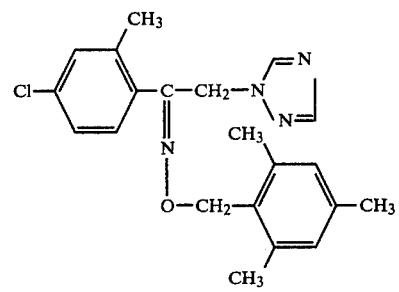

9. A fungicidal composition comprising as active ingredient a fungicidally effective amount of a compound, salt or complex according to claim 1 in admixture with a diluent.

10. A method of combating fungi comprising applying to the fungi, or to a habitat thereof, a fungicidally effective amount of a compound, salt or complex according to claim 1.

11. The method according to claim 10, wherein such compound is 1-(2,4-dichlorophenyl)-1-(2,3,6-trichloro-benzyloximino)-2-(1,2,4-triazol-1-yl)-ethane, 1-(2-chlorophenyl)-1-(2,4,6-trichloro-benzyloximino)-2-(1,2,4-triazol-1-yl)-ethane, 1-(2-chlorophenyl)-1-(2,4,6-trimethyl-benzyloximino)-2-(1,2,4-triazol-1-yl)-ethane, 1-(2,4-dichlorophenyl)-1-(2,4,6-trimethyl-benzyloximino)-2-(1,2,4-triazol-1-yl)-ethane or 1-(4-chloro-2-methylphenyl)-1-(2,4,6-trimethyl-benzyloximino)-2-(1,2,4-triazol-1-yl)-ethane.

* * * * *